United States Patent
Crawforth et al.

[11] Patent Number: 5,986,761
[45] Date of Patent: Nov. 16, 1999

[54] LASER-BASED INSPECTION TOOL FOR DISK DEFECTS AND CURVATURE

[75] Inventors: Linden Crawforth; Wayne Isami Imaino; Anthony Juliana, Jr.; Milton Russell Latta, all of San Jose; Hal Jervis Rosen, Los Gatos, all of Calif.

[73] Assignee: Internatioanl Business Machines Corporation, Armonk, N.Y.

[ * ] Notice: This patent is subject to a terminal disclaimer.

[21] Appl. No.: 09/110,925

[22] Filed: Jul. 6, 1998

[51] Int. Cl.$^6$ .................................................. G01B 11/30
[52] U.S. Cl. ............................................................ 356/371
[58] Field of Search ...................................... 356/371, 376

[56] References Cited

U.S. PATENT DOCUMENTS

| | | | |
|---|---|---|---|
| 3,885,875 | 5/1975 | Rosenfeld et al. | 356/371 |
| 4,125,317 | 11/1978 | Gordon et al. | 356/376 |
| 4,332,477 | 6/1982 | Sato et | 356/371 |
| 4,427,295 | 1/1984 | Nishiyama | 356/371 |
| 5,581,353 | 12/1996 | Taylor | 356/381 |

*Primary Examiner*—Richard A. Rosenberger
*Attorney, Agent, or Firm*—Thomas R. Berthold

[57] ABSTRACT

A laser-based inspection tool (LIT) for disks that allows simultaneous inspection of disk surfaces for defects and curvature. The laser beam is directed by a rotating scanner, such as a rotating polygon mirror, to the input of a telecentric lens assembly that provides an output beam parallel to its optical axis as the beam is being scanned. The output beam from the telecentric lens strikes the disk surface substantially perpendicularly. The beam is then reflected from the disk surface and passes back through a collection lens to the sensing surface of an optical detector. The detector outputs analog signals that represent the X and Y positions on the sensing surface where the reflected light beam is incident, which thus correspond to the slope of the disk surface at the point where the laser beam was incident. A mechanical disk lifter moves the disk in a plane parallel to the disk surface so that different scan lines can be generated on the disk surface. A processor, such as a personal computer, receives the output signals from the detector and calculates the slope values, and from the slope values, the curvature of the disk surface. A large number of points on each scan line are sampled, and a large number of scan lines are generated, so that the disk surface curvature can be calculated at various locations and over various ranges of the disk surface. The large number of sample points and the rapid calculation of slope values enables the shape of disk surface defects to be determined, which allows the disk defects to be classified as pits or bumps.

6 Claims, 8 Drawing Sheets

5,986,761

LASER-BASED INSPECTION TOOL FOR DISK DEFECTS AND CURVATURE

RELATED APPLICATION

This application is related to pending application Ser. No. 08/840,351, filed Apr. 28, 1997.

FIELD OF THE INVENTION

The invention relates generally to laser-based tools for obtaining data on surface features of substrates by optical means, and more particularly to such a tool for determining both the shape of defects on disk surfaces and the curvature of disk surfaces.

BACKGROUND

Magnetic and optical disks require smooth flat surfaces with extremely low defect rates to function properly. A typical magnetic disk comprises a substrate on which multiple layers of various materials are deposited. For example, a glass or aluminum substrate might be coated with thin films of Cr as an undercoat, a cobalt alloy magnetic layer, and a hydrogenated carbon overcoat. Depending on the stage of the process, these surfaces are not necessarily uniform. For example, a small circular band on the surface of the disk may be textured using a laser to form microscopic bumps. This textured region is intended to provide a low stiction area for the sliders to rest during nonoperating periods. In addition to intentional variations, there may be undesirable curvature as well as various types of defects. As the disks progress through the manufacturing process, various tests and inspections are used to detect defective disks so that they may either be reworked or discarded. In addition to visual inspections, a disk may be subjected to magnetic read/write tests. However, due to high capacities of magnetic disks, it is typically not practical to magnetically test each bit which can be stored on the disk. Laser surface inspection of the disks, if sufficiently precise, may actually be superior to current magnetic tests in detecting defects. Magnetic defects are usually associated with visible defects, but the visible defects can be detected more efficiently through laser inspection even though the laser spot size is considerably larger than the area in which a bit can be recorded. Thus, laser inspection allows greater test coverage of the disk in a cost-effective manner.

It is also desirable to inspect the disk substrate before any coatings or additional processing steps are added. If disk substrates with undesirable curvature and/or surface defects can be detected at this stage, a great savings can be realized by not incurring the costs of additional processing on defective parts. In addition it is desirable to be able to determine the shape or geometry of physical defects for the purpose of classifying disk defects by type and distinguishing real defects from dust particles.

What is needed is a laser-based surface inspection tool for determining both the shape of defects on disk surfaces and the curvature of disk surfaces at various stages in the disk manufacturing process.

SUMMARY OF THE INVENTION

The invention is a laser-based inspection tool (LIT) for disks that allows simultaneous inspection of disk surfaces for defects and curvature. The laser beam is directed by a rotating scanner, such as a rotating polygon mirror, to the input of a telecentric lens assembly that provides an output beam parallel to its optical axis as the beam is being scanned. The output beam from the telecentric lens strikes the disk surface substantially perpendicularly. The beam is then reflected from the disk surface and passes back through a collection lens to the sensing surface of an optical detector. The detector outputs analog signals that represent the X and Y positions on the sensing surface where the reflected light beam is incident. These X and Y values thus represent deviation of the disk surface from perfect flatness, i.e., slope, at the point on the scan line where the laser beam was incident. A mechanical disk lifter moves the disk in a plane parallel to the disk surface so that different scan lines can be generated on the disk surface. A processor, such as a personal computer, receives the output signals from the detector and calculates the slope values, and from the slope values, the curvature of the disk surface. A large number of points on each scan line are sampled, and a large number of scan lines are generated, so that the disk surface curvature can be calculated at various locations and over various ranges of the disk surface. This allows a wide variation of disk rejection criteria to be used. Also, the large number of sample points and the rapid calculation of slope values enables the shape of disk surface defects to be determined, which allows the disk defects to be classified as pits or bumps. The LIT includes an A-side and an identical B-side so that both surfaces of the disk can be inspected simultaneously.

For a fuller understanding of the nature and advantages of the present invention, reference should be made to the following detailed description taken together with the accompanying figures.

DETAILED DESCRIPTION OF THE PREFERRED EMBODIMENT

The preferred embodiment of the invention will be described in relation to a laser-based inspection tool for inspecting the planar surfaces of disks for use in disk drives. The inspection may be performed on substrates or finished disks, and is preferably performed on both surfaces of the disk simultaneously. The laser inspection tool (LIT) is general in that it can be used to inspect any sufficiently smooth flat surface at any stage of the process; therefore, it could be used to inspect raw or initial glass or aluminum substrates, aluminum substrates after nickel-phosphorous coating, or finished disks. The LIT uses low-angle reflected light rather than scattered light from the surface to simplify the design, to allow absolute reflectivity measurements if desired, and to aid in the detection of certain types of disk defects such as stains which do not effect the scattering of the light. Stain detection is accomplished through the use of derivative analysis of the reflected light to detect the change in the reflectivity of the surface associated with a disk stain. The system is designed to preserve both the polarization and the wave vector of the reflected light which allows it to be used with minor modifications in a broad range of applications. Using a stable laser, low-noise detectors, and sufficiently high-resolution, analog-to-digital (A/D) converters, it is possible to detect a change in reflectivity of approximately 0.1% using the LIT. Since the surfaces of the disks are extremely sensitive to physical contact, the LIT uses a mechanical lifter which, without clamping or spinning, moves the disk through the laser scan lines to allow the entire surface on each side of the disk to be scanned. Inspection or test systems which require the disks to spin are complex and increase the risk of damage to the disk. The line scanning is performed using a rotating polygon mirror (scanner) which also captures the beam reflected from the disk surface. As the disk is lifted into the scanning area by the mechanical lifter, it passes through a pair of air knives which blow loose particles from both surfaces.

Figure 1:
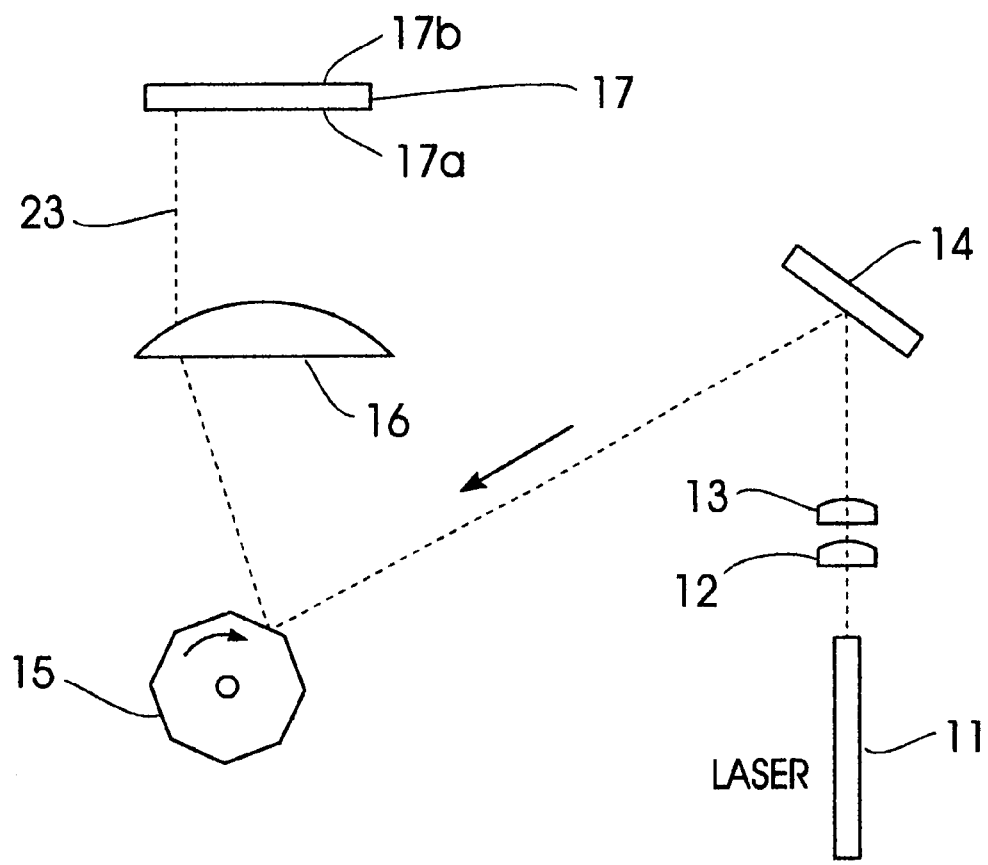
FIG. 1 shows the optical elements in the path from the laser source to the surface to be inspected.

FIG. 1 shows the optical path elements for the optical system of one channel (the A channel) of the LIT from the laser source 11 to the disk 17 and the disk surface to be inspected 17a in a preferred embodiment. The elements in the second channel (the B channel) for inspecting the other surface 17b are identical, but are preferably arranged in a mirror image of the A channel elements and in the same plane. The A and B channels can be assembled on a single baseplate. The choice of low-power laser is not critical, e.g., GaAs, HeNe, etc. are acceptable, but it is preferable that the wavelength be in the visible spectrum for aiding alignment. A few milliwatts of power is sufficient. Since high sensitivity to an absolute amount of reflected light is a goal in the design of the LIT, it is important to select a laser, e.g., HeNe, to minimize noise which might be injected into the system through laser instability. In the preferred embodiment, separate lasers are used for each channel, but it is also possible to use a single laser source with a beam splitter. Lenses 12 and 13 form a telescope (beam expander) which is used to expand the beam 23 (the incident beam). The term "incident beam" (or A beam to specify the A channel) will be used to refer to all segments of the laser beam from generation at the laser 11 along the path to the surface of the disk being inspected (or as will be noted later as an optional calibration mirror). Steering mirror 14 reflects the beam onto the rotating polygon scanner 15 which reflects into the telecentric lens assembly (TLA) 16. The TLA acts to keep the laser beam incident at a constant, nearly perpendicular angle as the beam scans across the disk. The TLA is designed to have a very flat field curvature through the scanning line to keep the spot size sufficiently constant for accurate detection. The figure shows the polygon scanner 15 rotating in a clockwise direction which will cause the incident beam to sweep from left to right across the TLA, and in turn to scan a line across the planar surface of the disk. Each mirrored facet of the polygon corresponds to one scan line across the disk. The choice of a polygon scanner is preferred, but other scanning means, such as a galvonometer mirror, could be used. The polygon scanner 15 is shown as having eight mirrored facets, so as to form a hexagon, but the polygon scanner may have more or fewer facets. The view of FIG. 1 can be considered to be a top view which shows only the top edge of the disk or other item having the planar surface to be inspected. The TLA should have a usable optical scan line which is at least equal to, and preferably slightly longer than, the desired scan length. A laser spot size on the disk of approximately 50 microns in diameter provides sufficient resolution for detecting defects in current disks. Smaller spot size can be used to increase the maximum resolution of the system if desired by altering the focal lengths of the telescope lenses.

Figure 2:
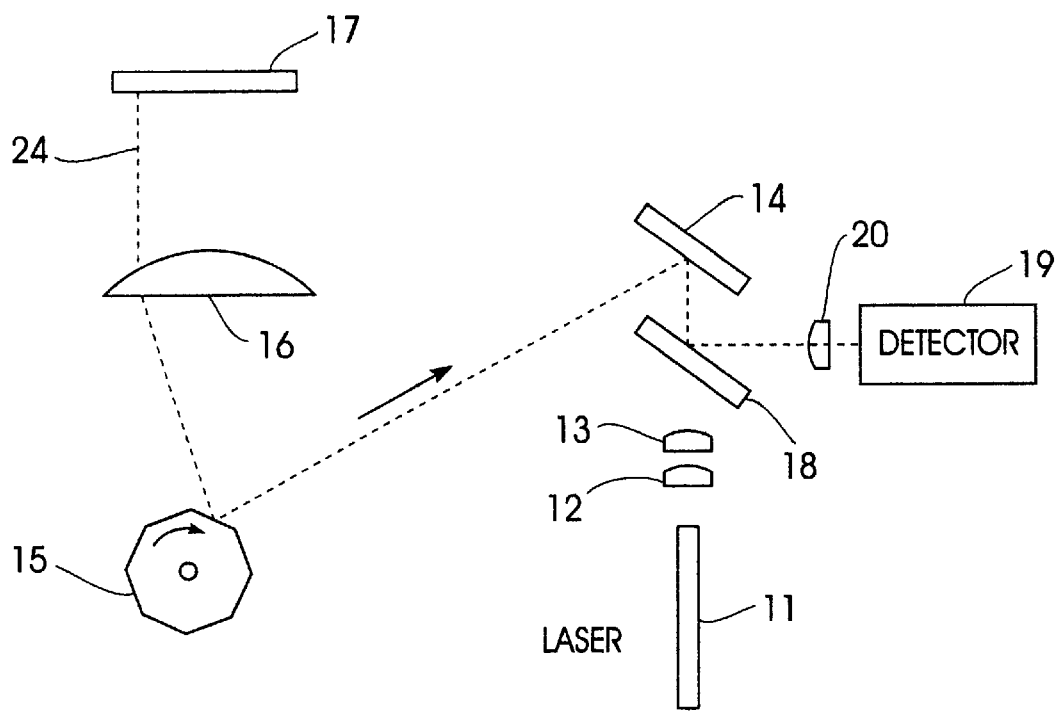
FIG. 2 shows the optical elements in the path for the reflected laser light from the surface being inspected.

FIG. 2 shows the optical elements in the path for the reflected beam 24 from the surface being inspected. The term "reflected beam" (or A/R beam) will be used to refer to all segments of the beam which are reflected from the object's surface as it follows the path to the detector. The surface of the object 17 reflects a portion of the incident beam to form a reflected beam 24 which follows a path back through the LIT, which is slightly offset from the path of the incident beam. (Note: The described embodiment inspects the planar surfaces of disks, but nonplanar surfaces could be inspected using the system if the nonplanarity is no more than a few degrees.) The reflected beam passes through the TLA 16 and is reflected by the scanner 15 back to mirror 14. Because the path of the reflected beam is offset from the incident beam, the reflected beam strikes capture mirror 18 which diverts the reflected beam through lens 20 which reduces the spot size of the beam striking detector 19. The detector is preferably a silicon detector which produces an analog signal which is a function of the amplitude of the reflected beam. The detector should have very low noise to preserve the sensitivity of the system. The LIT may function by detecting only relative shifts in the reflected beam as it scans across the surface and as the surface is translated under the beam, but it is advantageous to detect absolute reflectivity. The use of reflected light for inspection rather than scattered light allows a simplified approach and avoids the problems involved in trying to capture all of the scattered light. In addition, the use of reflected light allows detection of absorption changes and defects associated therewith.

Figure 3:
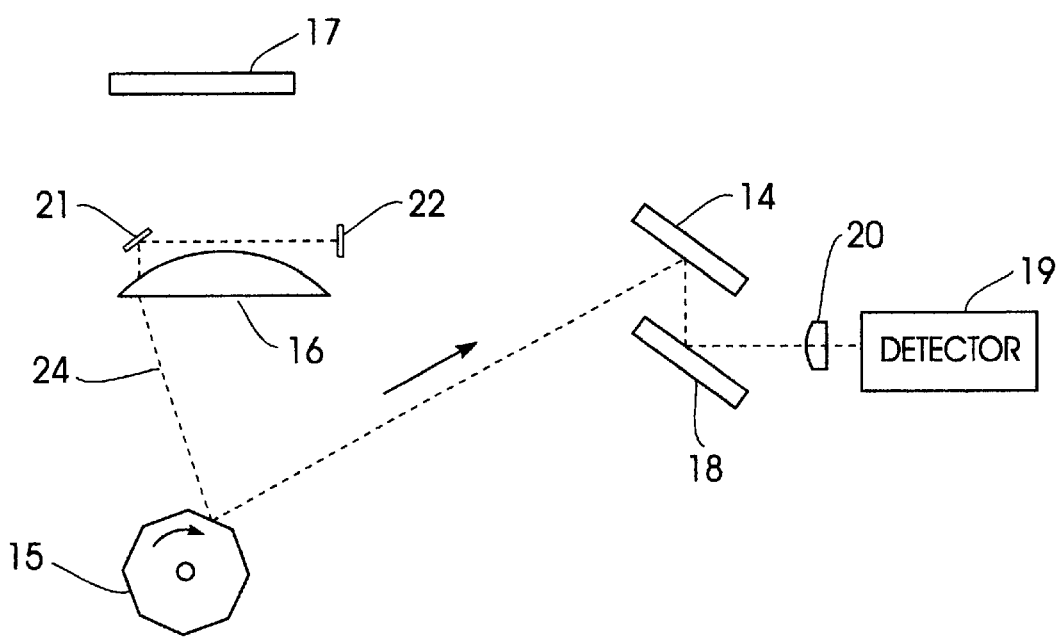
FIG. 3 shows the optical elements in the path for the reflected laser light from the calibration mirrors.

FIG. 3 shows an optional feature which provides a start of the scan signal and allows the detector to be calibrated to measure the absolute amplitude of the reflected beam. Measurement of the absolute reflectivity allows an additional class of defects and/or characteristics to be detected and/or measured, thus enhancing the capability of the tool. Calibration mirrors 21 and 22 are arranged so that an initial portion of the scan line falls on mirror 21, which reflects the beam to mirror 22 which reflects the beam back to mirror 21 and back into the TLA along the path for the reflected beam as described above. The length of the path of the beams going to and from the calibration mirrors is set equal to the length of the beam paths to and from the surface 17 to prevent spot size change. This arrangement creates a reference signal from the detector for each scan line which signals the start of scan, and is also known to correspond to the maximum possible magnitude of the reflected beam. Alternatively, a mirror could be positioned adjacent to the object being scanned to allow the beam to strike the mirror during the scan, but positioning the calibration mirrors away from the disk as shown in FIG. 3 is preferable since it reduces the number of fragile components near the mechanical moving parts. Having the maximum reference signal for comparison allows the amplitude of the reflected beam from the disk to be converted to an absolute measure of reflectivity. The signal from the calibration mirrors can be used as a start of scan without using it as an absolute amplitude reference. Once the beam strikes the calibration mirror 21, the reflected beam will slew to its maximum value. This transition from no reflected beam to the maximum forms a sharp edge in the analog output of the detector which can be used as the start-of-scan signal. A fixed delay can then be used to gauge the approximate time at which the scan line will be at the first data point on the disk. To avoid having false triggering from the other transitions in the signal at the edges of the disk, the circuitry which detects the start-of-scan signal should delay resetting until the scan line has cleared the last edge of the disk.

Figure 4:
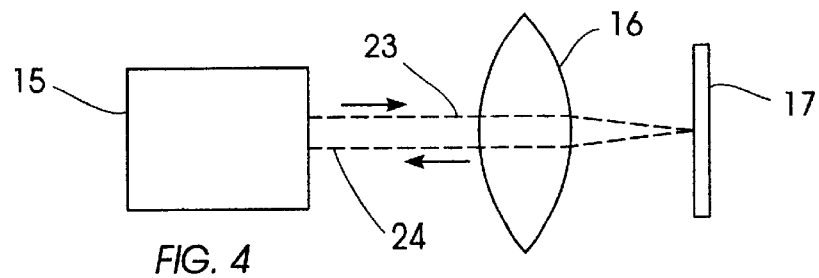
FIG. 4 shows the spatial relationship between the incident beam and the reflected beam between the surface and polygon mirror.

FIG. 4 shows the preferred spatial relationship between the incident beam and the reflected beam between the surface 17 and polygon mirror 15. As previously noted, the reflected beam 24 is offset from the incident beam 23 to allow the reflected beam to be routed to the detector. This is achieved by causing the incident beam to strike the surface at a slight angle which causes the reflected beam to come off at a slight angle as shown in FIG. 4. As an example, an offset angle of a few degrees over a 125 mm path results in a beam offset on the order of 5–10 mm which easily allows the reflected beam to be routed to a mirror which is by-passed by the incident beam. The telecentric aspect of the TLA causes the reflected beam 24 to be essentially parallel to incident beam 23 after the reflected beam has passed through the TLA. The optical axis of the TLA should ideally split the angle formed by the incident and reflected beam at the surface to minimize the effects of coma and spherical aberration due to the beam separation.

Figure 5:
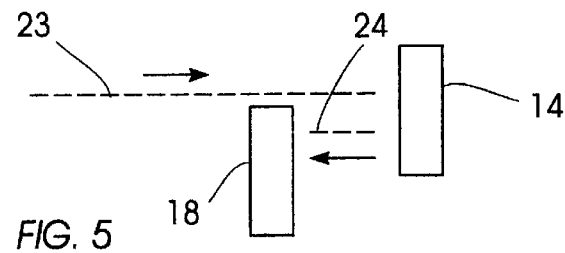
FIG. 5 shows the spatial relationship between the incident beam, the reflected beam, and the capture mirror.

FIG. 5 shows the spatial relationship between the incident beam and the reflected beam in relation to the capture mirror 18 and steering mirror 14. The incident beam 23 passes above the capture mirror 18 on its way to steering mirror 14. The reflected beam 24 is sufficiently offset to allow it to strike capture mirror 18 and to be routed to the detector. This arrangement is deemed superior to using a beam splitter with the signal losses associated therewith. It is feasible to allow the incident and reflected beam to be coincident until the reflected beam can be separated using an appropriate beam splitter, but the arrangement shown is deemed preferable. Beam splitters, which could be used if desired, include polarizing beam splitters, partially reflective beam splitters, or pellicle beam splitters.

Figure 6:
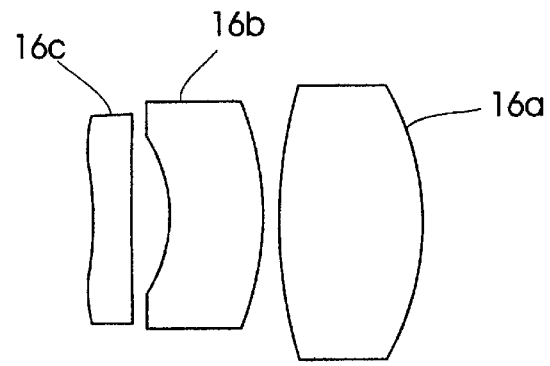
FIG. 6 shows a representative three-lens implementation of the telecentric lens assembly.

The TLA characteristics of the TLA 16 are tailored to the specifics of the application and particularly to the size of the surface being inspected. One standard size of disk for use in disk drives is 95 mm in diameter. For such a surface, the design of the TLA could be specified for the wavelength of the laser being used as a field of 105 mm, focal length of 125 mm, telecentricity of<0.5 degrees, and field curvature of <1.0 mm. FIG. 6 illustrates a three-element (elements 16a, 16b, 16c) spherical lens implementation which can be used to meet these requirements. Other implementations (including a single lens) may be used. An optical configuration which is capable of scanning 95 mm disks is also capable of being used to scan smaller disks. When smaller objects are being scanned, it may be desirable to increase the sampling rate in order to obtain the same number of pixels for the smaller object.

Figure 7:
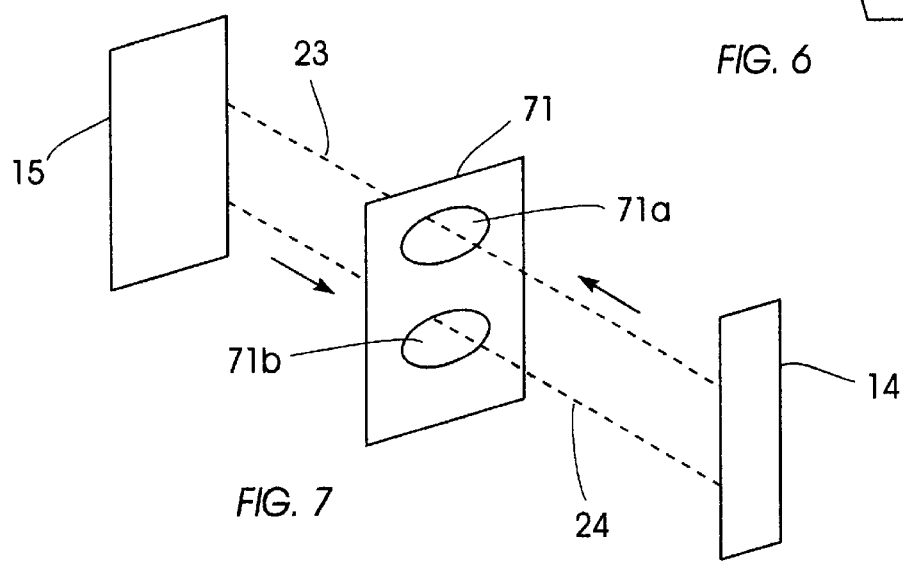
FIG. 7 shows an alignment aperture mask.

FIG. 7 shows an optional aperture mask 71, having apertures (holes) 71a and 71b, which is positioned between scanner 15 and mirror 14 (see FIG. 2) so that the incident beam 23 passes through aperture 71a and reflected beam 24 passes through aperture 71b. The aperture mask is made from opaque material and the apertures are sized to limit the cone of scattered light that passes through. Limiting the cone of the reflected beam is more important than for the incident beam. The reflected beam cone size should be limited to removing some of the near-forward scattered light to improve the sensitivity of the detector to reflected light. The size of the aperture for the reflected light should be selected empirically for the particular application by scanning a surface feature known to produce near-forward scattered light, e.g., laser texture bumps on disks. The aperture should not be overly restrictive, however, since variation in the polygon faces, etc. will cause some tolerances to exist in the reflected beam. Using an aperture of approximately six times the diameter of the beam in the arrangement shown was found to result in a superior detection capability for the laser texture zone. The masking of the near-forward scattered light can be performed at various points in the path of the reflected beam, e.g., at the detector, but the position of the aperture mask as shown has the additional benefit of providing an aid for coarse alignment of the beams which should be positioned in the center of the apertures. Optionally, a removable translucent member may be placed over the apertures to enhance the visibility of the beam position during alignment. Various other alignment features and aids may be incorporated into the design of the LIT. For use in a manufacturing environment, it is important that alignment be easy to obtain and to maintain. In a two-channel implementation, the disk must be centered between the two TLAs and be perpendicular to the horizontal axis of the system. The position of the disk holder with respect to the optics board is adjusted, then the distance position along the mounting rail of the TLAs is adjusted. Preferably, several of the components in the optical path will have X-Y adjustments, but it is not required that they all have adjustments. The lenses 12, 13 comprising the telescope are likewise mounted on rails to allow the distance between them to be adjusted to control spot size. At least one of the lenses in the telescope should preferably have a fine position adjustment. The apertures in the aperture mask may also be used during the finer alignment process by positioning target plugs in the apertures which have small diameter alignment holes, e.g., 1 mm in diameter, positioned at the central point where the beams are properly aligned. One or more similar targets with alignment holes may be used in the path from the laser to the steering mirror. If the laser and the telescope lenses are mounted on an optical rail, one or more targets with alignment holes can be placed on the rail and moved along the rail if desired to aid in the X-Y alignment of the laser. The approximate alignment of the beams can be observed visually since misalignment will reduce the intensity of the beam passing through the small holes. After coarse alignment has been achieved, the amplitude of the beam as measured by the detector 19 provides a precise aid for alignment of the entire path. The X-Y adjustments of the laser, the steering mirror, etc. are used to achieve maximum amplitude of the output signal at the detector from a reference disk having at least a portion which is used as a defect-free standard. The TLA 16 determines the spot focusing and telecentricity of the beam. Telecentricity is determined by the spacing of the TLA to the polygon 15, and is set using the scan lens micrometer which translates the TLA along the axis between the polygon and the disk. The input beam collimation of the incident beam entering the TLA is set by adjusting the spacing between lenses 12 and 13 of the telescope. The circularity of the return beam after reflection from the polygon is a function of the telecentricity and can be used during alignment. Spot size should be reasonably constant through a scan so spot size should be measured across the scan field using a spot size measuring instrument positioned in the scan plane at multiple scan positions. If the deviation in spot size is too large, additional alignment is needed.

Polygon Synchronization

Figure 8:
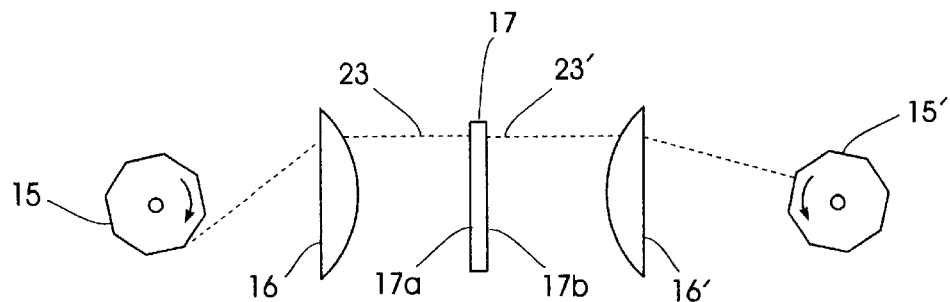
FIG. 8 shows the polygon scanner orientations in a two-channel embodiment.
Figure 9:
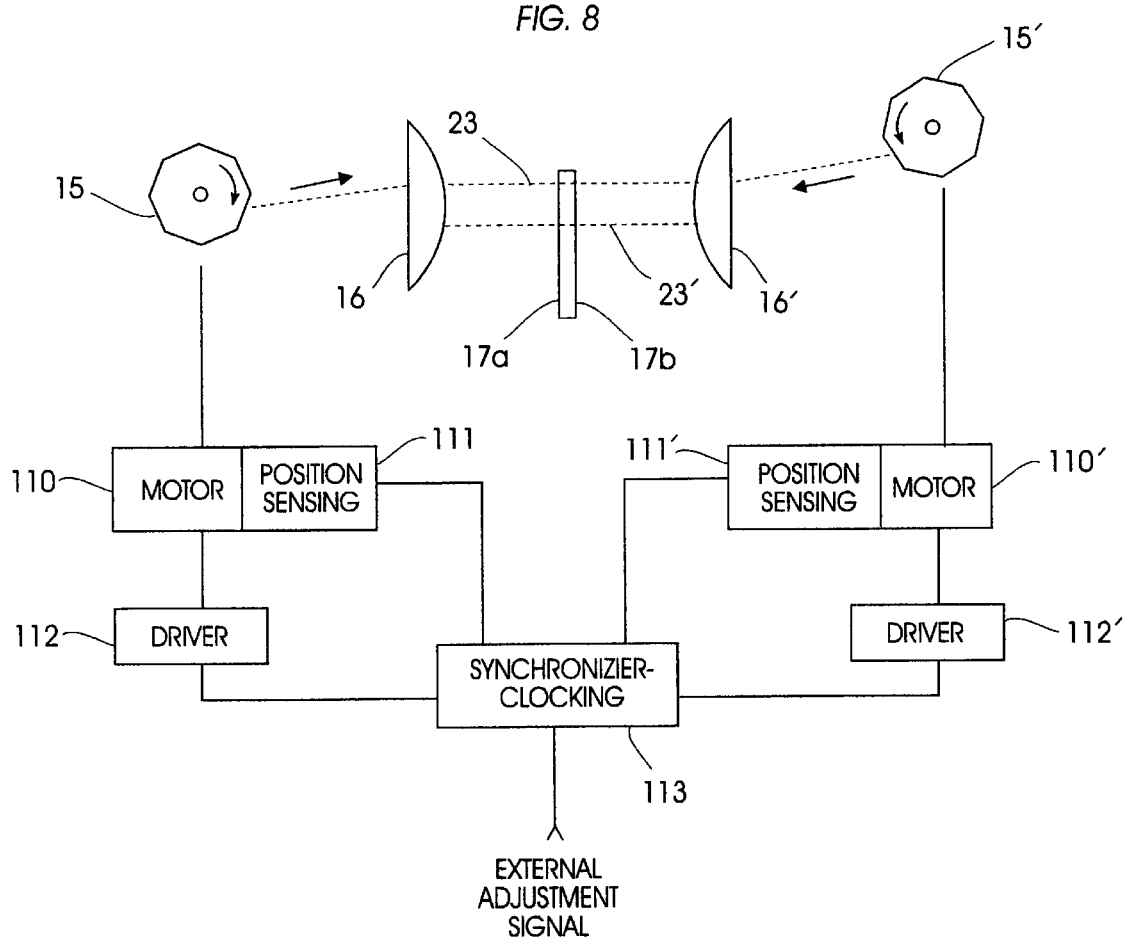
FIG. 9 illustrates a control system for synchronizing and offsetting the rotation of the polygon scanners.

In a two-channel implementation of the invention, i.e., a LIT which inspects both planar surfaces of a disk simultaneously, there are several options on how the A and B beams can be spaced and coordinated with each other. Interference between the channels will occur when the beams pass through the central hole in the disk unless steps are taken to prevent it. A similar problem might arise if the LIT is being used to inspect any object having holes and/or transparent portions. The polygons can be arranged to rotate in a common direction which will result in the scan on each side of the disk proceeding in opposite directions and crossing in the center of the scan area. When the beams cross, there will be crosstalk as the beam from the opposite channel reaches the detectors. One arrangement to minimize interference has the B beam vertically displaced from the A beam, but this causes difficulties in building the tool and coordinating the data. A preferred arrangement is shown in FIG. 8. FIG. 8 shows the polygon scanner orientations in a two-channel embodiment where the polygons 15, 15' are coplanar, but spin in opposite directions which results in the two beams 23, 23' maintaining a fixed relationship to each other as they scan. In a preferred embodiment, the rotational position of the two polygon mirror scanners is synchronized. This will allow the beam from the A side optics to be transmitted to the B side where it is "descanned" by the polygon mirror. FIG. 9 illustrates a control system for synchronization and offset of the polygons. Beams 23, 23' are shown passing through the hole in the disk. The beams are only shown up to the TLAs 16, 16' but each will, of course, pass through the transparent lenses and be reflected from the polygon facet. The separation between the beams is shown greatly exaggerated so that the offset is clearly visible. The polygons are rotated by DC motors 110, 110' which have integral position sensing units 111, 111' which can provide index pulses as well as a binary value indicating the angular position of the motor. The positional signals are fed back into the synchronizer/clocking unit 113. This provides signals to the motor drivers 112, 112' which control the speed and phase of the motors. Using the position feedback and an external input, the synchronizer/clocking unit retards or advances the phase of one of the motors (e.g., motor 110') to allow the magnitude of the offset between the two motors to be controlled while maintaining the same rotational speed. The external input signal can be as simple as a pulse generated by an operator pressing a switch which causes the phase to advance a few microseconds for each pulse. One convenient way to set the offset is to adjust for zero motion of the descanned signal. An operator could do this by observing an oscilloscope trace of the output of the detector and bumping the phase switch until the signal change with time is essentially zero.

Figure 10:
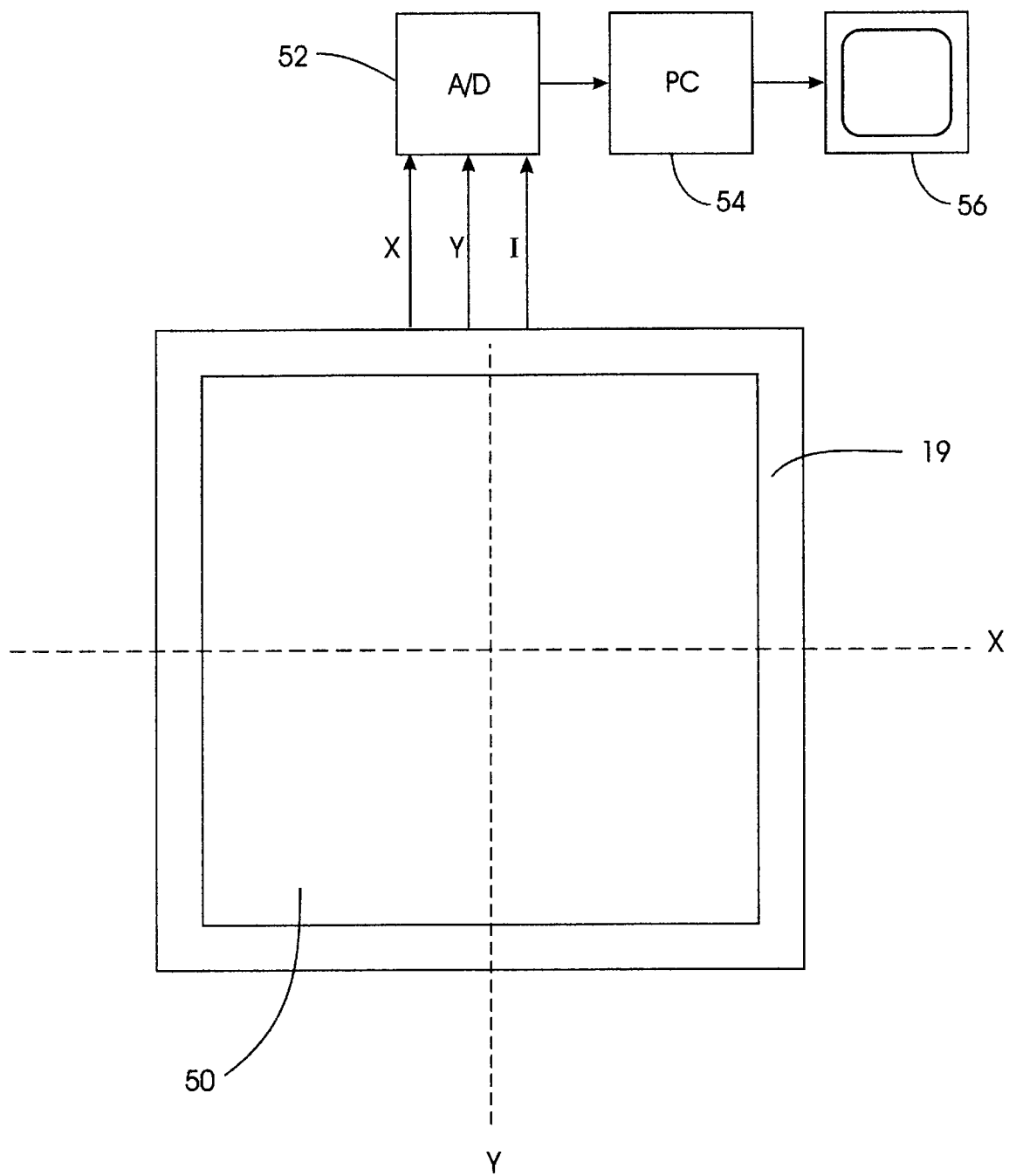
FIG. 10 is a block diagram of the optical detector and its connection to a personal computer (PC) for displaying disk curvature and defect shape information.

Preferred TImplementation of the LIT for Measurement of Disk Curvature and Defect Shape Referring now to FIG. 10, the optical detector 19 is a conventional position sensing optical detector, such as PIN-SC/50 available from UDT (United Detector Technology, Santa Monica, Calif.), that provides three analog outputs X, Y and I. The X output is a measure of the location on the detector surface 50 along the X direction where the reflected beam strikes, the output Y is a measure of the location on the detector surface 50 along the Y direction where the reflected beam strikes, and the output I is the intensity of the reflected beam striking surface 50. The detector outputs are sent to an analog-to-digital (A/D) converter 52 and then to a central processor, such as a personal computer (PC) 54 which is connected to any suitable output device, such as a video display 56. If the beam from TLA 16 (FIG. 2) strikes the disk surface 17a precisely perpendicularly then the reflected beam will strike surface 50 of detector 19 precisely in the center and the X and Y outputs will be zero, thus representing that there is no slope in either the X or Y direction at the point where the beam struck disk surface 17a.

Figure 11:
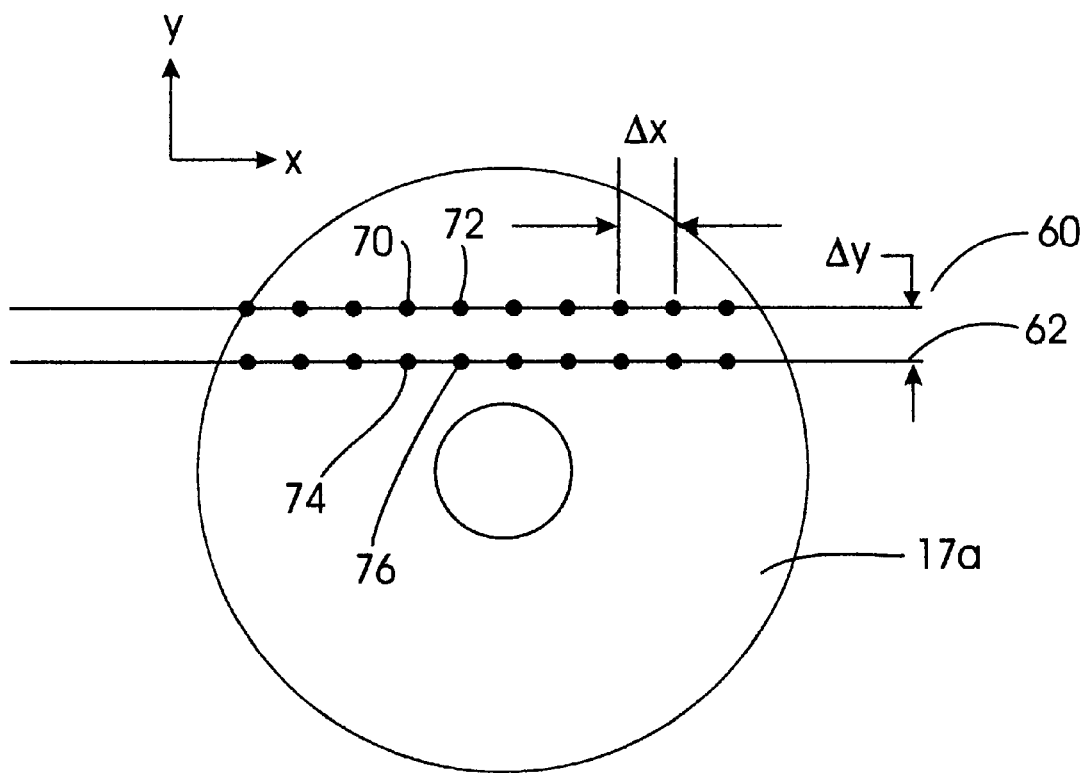
FIG. 11 is an illustration of a disk surface showing two scan lines with discrete points where disk slope s computed for calculation of disk curvature.

FIG. 11 shows two consecutive scan lines 60, 62 across the disk surface 17a representing the passage of the laser beam caused by polygonal mirror 15 (FIG. 2). A series of points, such as points 70, 72 are shown on line 60 and points 74, 76 are shown on line 62. Each point represents a location on the disk surface 17a that will provide discrete sample outputs X(n), Y(n), I(n) from detector 19. The adjacent points along a scan line are separated by a distance $\Delta X$. After the laser has scanned along line 60, the disk lifter raises the disk 17 a distance $\Delta Y$ and the laser then scans along line 62. In the preferred embodiment the distances $\Delta X$ and $\Delta Y$ are equal. There are typically a large number of scan lines, e.g., 2000, and sample points per line, e.g., 2000, for each disk surface. For each point along a scan line the disk surface will have an X and a Y slope value, $\theta_x$ and $\theta_y$, respectively, along the X and Y directions. Zero slope everywhere indicates perfect flatness. The X and Y outputs of detector 19 are used by the PC 54 to calculate $\theta_x$ and $\theta_y$ for each point along the scan lines as follows:

$$\Theta_X = 2X \frac{F2}{F1(F2-D)}$$

$$\Theta_Y = 2Y \frac{F2}{F1(F2-D)}$$

The term F1 is the focal length of TLA 16, the term F2 is the focal length of collection lens 20, and D is the distance between the collection lens 20 and the surface 50 of detector 19.

The disk curvature is the derivative of the slope. Thus the curvature of the disk surface 17a along the X direction between points 70, 72 is the difference between the two values of $\theta_x$ at these points, divided by $\Delta X$, or:

$$\frac{\Theta_X(72) - \Theta_X(70)}{\Delta X}$$

Similarly the curvature of the disk surface 17a along the Y direction between points 74, 70 is the difference between the two values of $\theta_y$ at these points, divided by $\Delta Y$, or:

$$\frac{\Theta_Y(72) - \Theta_Y(70)}{\Delta Y}$$

The calculated values of disk surface curvature are used to reject a disk being inspected. Various types of rejection criteria are possible because of the large number of slope values taken over the disk surface. For example, the disk may have a curvature specification at a particular radius, such as the middle of the data band. Thus the curvatures calculated over a portion of a scan line about the radial location would have to be below the allowed specification for all scan lines. Alternatively, or in addition, the curvature could be calculated along any portion of a scan line and the disk rejected if any measured curvature was outside the specification. Because the values of $\theta_x$ and $\theta_y$ are available for the entire disk surface, e.g., 4 million data points if there are 2000 scan lines with 2000 sample points per line, the PC 54 can also generate a 3-dimensional like image of the disk surface on display 56 to allow the operator to visualize the shape of the entire disk surface.

Figure 12:
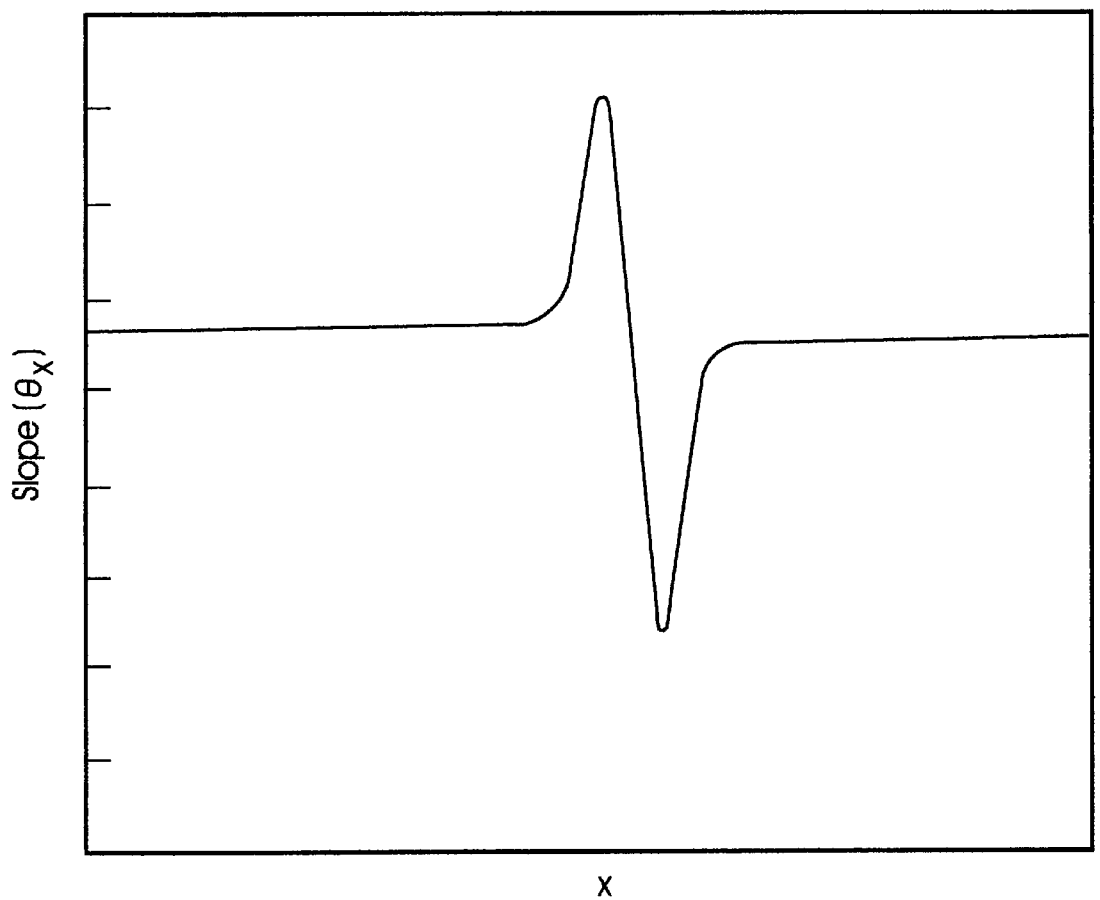
FIG. 12 is a graph of disk slope along a scan line illustrating the presence of pit in the disk surface.

The present invention also allows a determination of the shape or geometry of a defect because of the rapid calculation of slope. This information can be used to classify a defect as a pit or a bump. All pits, which are typically small scratches, are real defects, while bumps may be either real defects, such as surface asperities, or removable particles, typically dust particles. Shown in FIG. 12 is a graphical output of slope as a function of X position along a scan line displayed on display 54. The upper and lower peaks represent a rapid increase in slope followed by a rapid decrease in slope. This shape of signal output has been correlated with a pit, thus representing a real defect on the disk surface. A bump or particle on the disk surface would produce an output inverted from that in FIG. 12. With the present invention, if an unacceptable number of bumps are detected the disk lifter can move the disk through an air knife to remove dust particles and the disk can then be inspected again to determine if the defects were dust particles or asperities.

In the present invention, the determination of disk surface curvature occurs simultaneously with inspection of disk defects by the LIT because the detector 19 also provides an intensity measurement I at each sample point. In addition, because the LIT has identical A and B inspection sides, both surfaces of the disk can be inspected for curvature simultaneously.

Figure 13:
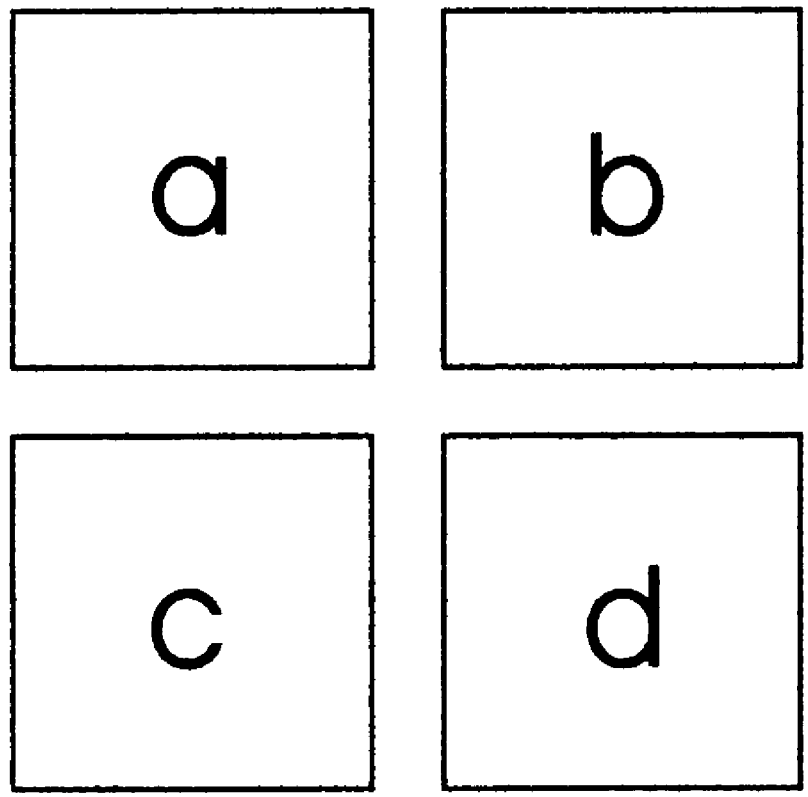
FIG. 13 is a illustration of the detection surface of a conventional quadrant detector which may also be used with the present invention.

An alternative detector for use with the present invention is a conventional quadrant detector having a sensing surface as shown in FIG. 13. Such a quadrant detector is a PIN-Spot/4D available from UDT. If A, B, C, D represent the output signals from the quadrants labeled a, b, c, d in FIG. 13, then the sum of these outputs (A+B+C+D) yields the intensity of the reflected light. The combination of outputs A+B−(C+D) yields a signal proporational to the position of the beam in the vertical or Y direction on the detector and similarly the combination of outputs A+C−(B+D) yields a signal proportional to the position of the beam in the horizontal or X direction on the detector. The equations described above for determining $\theta_x$ and $\theta_y$ as functions of X and Y also apply to the quadrant detector.

While the present invention has been particularly shown and described with reference to the preferred embodiments, it will be understood by those skilled in the art that various changes in form and detail may be made without departing from the spirit, scope, and teaching of the invention. Accordingly, the disclosed invention is to be considered merely as illustrative and limited in scope only as specified in the appended claims.

What is claimed is:

1. An apparatus for determining curvature of the two surfaces of a disk comprising:

a laser for generating a laser beam, the laser beam being directed along a first optical path to the first surface of the disk;

a first rotatable polygon mirror located in the first optical path for scanning the beam along a line across a portion of the first disk surface;

a first telecentric lens assembly located in the first optical path between the first rotatable mirror and the disk for causing the beam to strike the first disk surface substantially perpendicular to the first disk surface during scanning of the beam;

a first light detector having a sensing surface for receiving a reflected light beam from the first disk surface during scanning, the first detector providing output signals representative of the locations on the sensing surface where the reflected light beam is incident, each output signal corresponding to a point along a scan line on the first disk surface;

a first processor coupled to the first light detector for calculating, from the output signals, the curvature of the first disk surface;

a second laser for generating a second laser beam, the second laser beam being directed along a second optical path to the second surface of the disk;

a second rotatable polygon mirror located in the second optical path for scanning the beam along a line across a portion of the second disk surface, the second rotatable mirror lying in a plane common with the first rotatable mirror and being rotatable in a direction opposite the direction of rotation of the second rotatable mirror;

means for synchronizing the rotation of the first and second rotatable mirrors;

a second telecentric lens assembly located in the second optical path between the second rotatable mirror and the disk for causing the beam to strike the second disk surface substantially perpendicular to the second disk surface during scanning of the second beam;

a second light detector having a sensing surface for receiving a reflected light beam from the second disk surface during scanning, the detector providing output signals representative of the locations on the sensing surface where the reflected light beam is incident, each output signal corresponding to a point along a scan line on the second disk surface;

a second processor coupled to the second light detector for calculating, from the output signals, the curvature of the second disk surface; and a disk lifter for moving the disk in a direction generally parallel to the disk surfaces after a scan line has been generated to enable additional scan lines to be generated on additional portions of the disk surfaces.

2. The apparatus of claim 1 wherein the first processor calculates from successive output signals the curvature of the first disk surface along an X direction corresponding to a scan line.

3. The apparatus of claim 2 wherein the first processor identifies pits in the first surface of the disk from the calculated disk surface curvature.

4. The apparatus of claim 2 wherein the first processor identifies bumps on the first surface of the disk from the calculated disk surface curvature.

5. The apparatus of claim 1 wherein the processor calculates, from output signals from two successive scan lines, the curvature of the first disk surface along a Y direction corresponding to a line generally perpendicular to the scan lines.

6. The apparatus of claim 1 wherein the output signals from the first detector are analog signals, and further comprising an analog-to-digital converter coupled between the first detector and the first processor.

* * * * *